United States Patent
Lindenberg et al.

[19]
[11] Patent Number: 6,053,941
[45] Date of Patent: Apr. 25, 2000

[54] STENT WITH AN END OF GREATER DIAMETER THAN ITS MAIN BODY

[75] Inventors: Josef Lindenberg, Wörthersee; Wolfram Schnepp-Pesch, Karlsruhe, both of Germany

[73] Assignee: Angiomed GmbH & Co. Medizintechnik KG, Karlsruhe, Germany

[21] Appl. No.: 09/020,386

[22] Filed: Feb. 9, 1998

Related U.S. Application Data

[63] Continuation of application No. 08/586,696, filed as application No. PCT/US95/01925, May 20, 1995, Pat. No. 5,716,393.

[30] Foreign Application Priority Data

May 26, 1994 [DE] Germany ............... 44 18 336

[51] Int. Cl.⁷ .................................................. A61F 2/06
[52] U.S. Cl. ........................................................ 623/1
[58] Field of Search ................... 623/1, 11, 12; 606/108, 191, 194, 195, 198

[56] References Cited

U.S. PATENT DOCUMENTS

| | | | |
|---|---|---|---|
| 4,733,665 | 3/1988 | Palmaz | 623/1 |
| 4,830,003 | 5/1989 | Wolff et al. | 623/1 |
| 4,994,066 | 2/1991 | Voss . | |
| 5,019,090 | 5/1991 | Pinchuk | 623/1 |
| 5,064,435 | 11/1991 | Porter . | |
| 5,104,404 | 4/1992 | Wolff | 623/1 |
| 5,195,984 | 3/1993 | Schatz | 623/1 |
| 5,197,978 | 3/1993 | Hess | 623/12 |
| 5,282,824 | 2/1994 | Gianturco | 623/1 |
| 5,330,500 | 7/1994 | Song . | |
| 5,354,308 | 10/1994 | Simon et al. . | |
| 5,354,309 | 10/1994 | Schnepp-Pesch et al. . | |
| 5,382,261 | 1/1995 | Palmaz . | |
| 5,466,242 | 11/1995 | Mori . | |
| 5,545,210 | 8/1996 | Hess et al. | 623/12 |
| 5,853,419 | 12/1998 | Imran | 606/191 |

FOREIGN PATENT DOCUMENTS

| | | | |
|---|---|---|---|
| 0274846 | 7/1988 | European Pat. Off. . | |
| 0540290 | 5/1993 | European Pat. Off. . | |
| 0556850 | 8/1993 | European Pat. Off. . | |
| 0 688 545 A1 | 12/1995 | European Pat. Off. | 623/1 |
| 1771719 | 10/1992 | U.S.S.R. . | |
| 2189150 | 10/1987 | United Kingdom . | |
| 93/17636 | 9/1993 | WIPO . | |
| 9317636 | 9/1993 | WIPO . | |
| 9417754 | 8/1994 | WIPO . | |
| 9112779 | 4/1995 | WIPO . | |
| 9509586 | 4/1995 | WIPO . | |

*Primary Examiner*—Mickey Yu
*Assistant Examiner*—Tram A. Nguyen
*Attorney, Agent, or Firm*—Antonelli, Terry, Stout & Kraus, LLP

[57] ABSTRACT

For the better anchoring of a stent in its use area within a vessel, in the case of a stent expandable from a radially contracted introduction state into a radially expanded position state and having a body with material areas in the form of ribs and gaps in the form of free spaces between the ribs, in the radially expanded state at least one front end of the stent has a greater radial extension than the remaining main stent body with the material areas of the body being relatively thin and without material crossing points as in knitted and braided structures.

10 Claims, 3 Drawing Sheets

STENT WITH AN END OF GREATER DIAMETER THAN ITS MAIN BODY

REFERENCE TO RELATED APPLICATION

This application is a continuation of application Ser. No. 08/586,696, now U.S. Pat. No. 5,716,393, filed Feb. 26, 1996, which is a 371 of PCT/US95/01925 filed May 20, 1995, and claiming priority of German application P 44 18 336.4 filed May 26, 1994. The disclosure of U.S. Ser. No. 08/586,696 is hereby incorporated by reference.

FIELD OF INVENTION

The invention relates to a scent for dilating and keeping open vessels, with a radially contracted state for introduction into the vessel and with a radially expanded state after introduction into the vessel.

BACKGROUND AND SUMMARY OF INVENTION

Such stents or implantable catheters to be introduced into a body cavity, a vessel or the like can be made from plastic or an inert metal, such as steel or nickel-titanium alloys. Such stents are also referred to as endovascular or endoluminal stents or endoprostheses. For example when dilating the ureter the stents are used in the prostate region in the case of benign prostate hyperplasia (BPH) or also in sclerotic blood vessels for dilating and keeping open the same. The stents have material areas and gaps between them. Thus, it is possible for the wall tissue of the organ kept open to grow round the stent. Stents can have a spiral construction or can be in the form of a helically wound coil. They can be made from woven or knitted wire or plastic material. Such stents can have memory properties, such as e.g. exist with certain nickel-titanium alloys (nitinol).

The problem of the invention is to ensure a secure anchoring of such a stent in the vessel to be dilated.

According to the invention the set problem is solved in the case of such a stent in that in the radially expanded state at least one front end has a greater radial extension than the remaining main body of the stent.

In the case of a stent, which is formed by ribs and free spaces left between the same, according to a preferred development of the invention in the vicinity of at least one front end of the stent the ribs have a greater length than corresponding ribs of the main stent body and in particular the length of the ribs in the front region can be 120 to 190% of the length of the ribs in the main stent region.

According to further preferred developments of the invention, in the front side areas the ribs extend radially further outwards than the ribs in the main stent area and the ribs in the front side area form a finite angle to the major axis of the stent.

The free spaces can either be diamond-shaped or honey-combed. The stent is preferably self-expanding and in a preferred development not solely due to elastic properties and introduction in a state under radial tension, but as a result of the fact that it is made from a memory metal.

In order to attain a greater bendability and flexibility of the stent, according to a further preferred development, between axially succeeding ribs are provided in part gaps and in part connecting areas. This is achieved by a higher flexibility than would be the case with a stent in which axially succeeding ribs were firmly interconnected in the connecting areas. There is also no cross-sectional deformation when bending under the action of vertical axial forces.

Due to the fact that the stent is constructed in single layer form, a high bendability is obtained without metal crossing points, such as is the case with knitted and braided structures and the like, which give rise to a greater material thickness. There can be a better growing in of the stent of the invention into the tissue. The risk of thromboses occurring, particularly in the vascular area is significantly reduced or virtually excluded.

In a preferred development, the connecting areas are circumferentially mutually displaced. This leads to the retention or obtaining of the desired axial strength (i.e. against compression and tension in the axial direction) in the case of bending resistance perpendicular to the axis.

According to further preferred developments the stent is made from a flat plate from which are cut slots for forming the gaps, the flat plates being connected together, particularly by welding, in the marginal areas after bending to a cylindrical contour and the free spaces are formed by slots after heat treatment.

Further advantages and features of the invention can be gathered from the claims and description of a preferred embodiment of the invention with reference to the drawings.

DETAILED DESCRIPTION OF DISCLOSED EMBODIMENT

Figure 1:
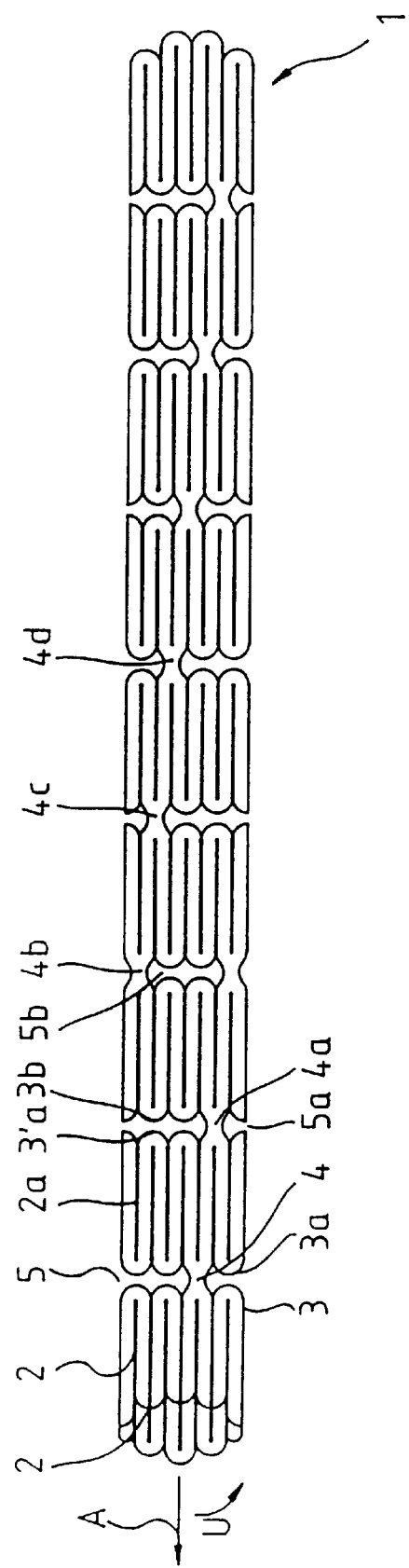
FIG. 1 is a preferred development of the stent according to the invention in its radially contracted low temperature or introduction state.

In its radially contracted state for introduction into the vessel to be dilated, the stent 1 according to the invention has a cylindrical shape or an outer contour as shown in FIG. 1. In the expanded state the stent 1 according to the invention has over the length L of its main body, i.e. its greatest length, a cylindrical outer contour. However, in the vicinity of its two front ends 1b, 1c, the stent according to the invention is radially expanded over the radial dimensions, i.e. the diameter D of the main body 1a, so that the stent 1 can be anchored with its radially expanded ends 1b, 1c on the vessel wall.

Figure 2:
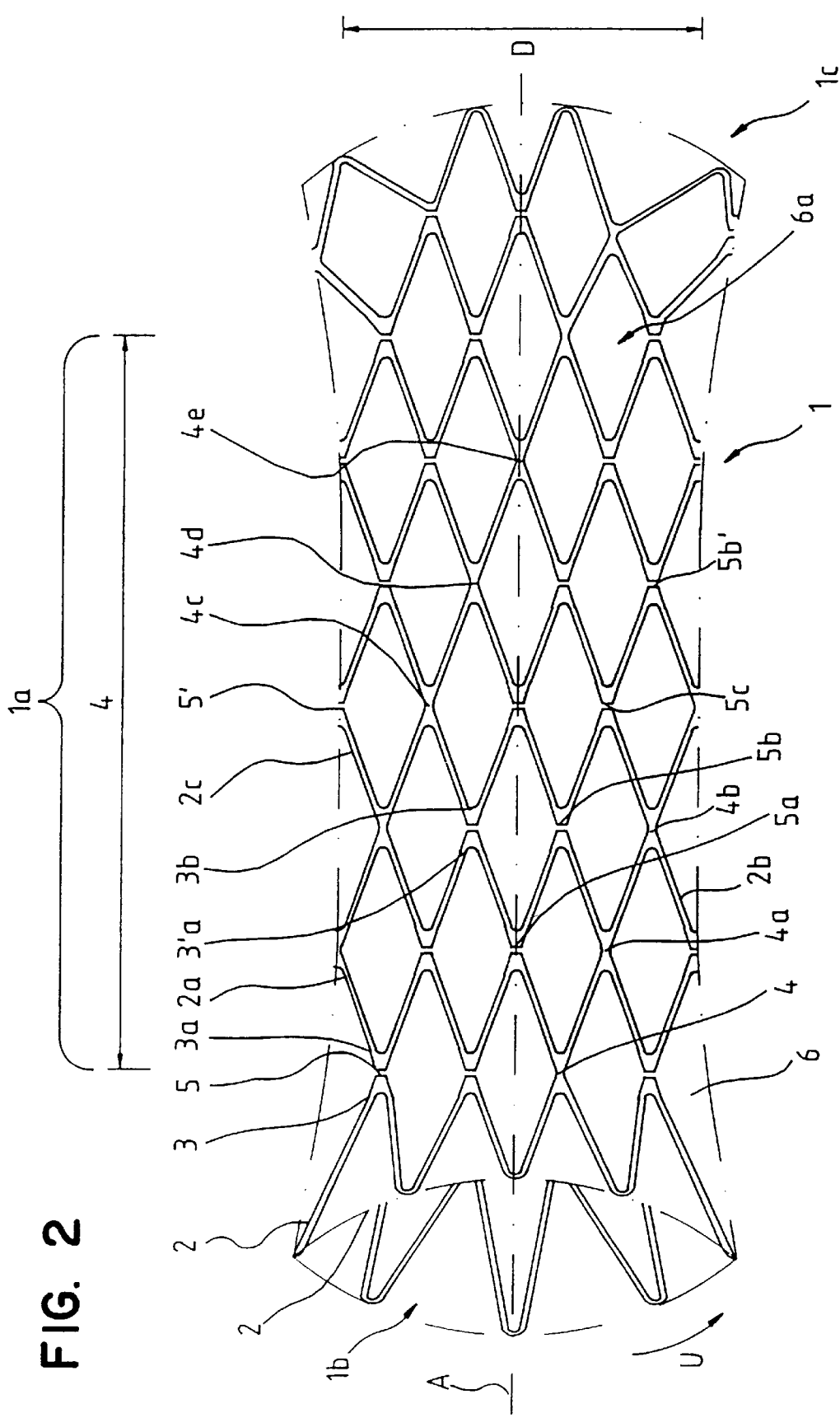
FIG. 2 shows the stent according to the invention in its radially expanded high temperature or use state.

As is in particular made clear by FIG. 2, the stent 1 according to the invention is formed from a plurality of meander paths arranged successively over the circumference of the stent 1 in the form of angularly interconnected ribs 2 or 2a or 2b in the connecting or tip regions 3, 3a, 3'a, 3b. In the circumferential direction the meander paths or ribs 2, 2a, 2b are so arranged that in each case facing, adjacent connecting or tip regions 3, 3a or 3'a, 3b of juxtaposed meander paths or ribs 2, 2a, 2b are axially aligned.

FIG. 2 also clearly shows that the axially succeeding meander paths formed by the ribs 2, 2a, 2b in the vicinity of their tip or connecting regions 3, 3a, 3'a, 3b are not interconnected by transitions 4, 4a, 4b, 4c, 4d, 4e but in the circumferential direction between such transitions 4 to 4d of two adjacent meander paths formed by the ribs 2, 2a are located several gads 5, 5', 5a, 5b, 5c 5b', etc. The transition areas 4 to 4d and gaps 5 to 5b' are jointly also referred to as nodal areas.

Considered in another way, the stent according to the invention can be formed by ribs 2, 2a, 2b and free spaces 6, 6a formed between them, the free spaces 6, 6a in the embodiment shown having the contour of a diamond, i.e. are bounded by four rib areas, but could also be shaped like a honeycomb, that being bounded by six rib areas. The nodal areas in this case are partly left as connections 4 to 4d, whereas in other areas they are split by the gaps 5 to 5b'. The connections or transitions 4 to 4d are not axially aligned, but are in each case angularly or circumferentially displaced.

The gaps 5 to 5b', etc. lead to a high flexibility of the stent according to the invention. It is in particular attained that the stent 1, on bending perpendicular to its longitudinal axis A and therefore bending of the longitudinal axis itself does not kink or bend in in the central area in such a way that it loses its cross-sectionally substantially circular contour and in the action direction of the forces is centrally pressed flat and perpendicular to the action direction of the forces is widened roughly in the centre of its longitudinal extension, as occurs with conventional stents, where all the facing, adjacent tip or connecting areas 3, 3a, etc. in axially juxtaposed meander turns are firmly connected by connecting areas or transitions 4, 4a. The connecting areas or transitions 4, 4a, etc. are constructed in one piece with the remaining parts of the stent, particularly the ribs 2, 2a, etc. and their adjacent tip or connecting areas 3, 3a.

FIG. 1 shows that the substantially diamond-shaped free spaces (FIG. 2) formed between the ribs 2, 2a, etc. of the meander paths in the high temperature position taper to slots in the low temperature or introduction position and the ribs 2, etc. of the meander paths are substantially parallel to one another.

Figure 3:
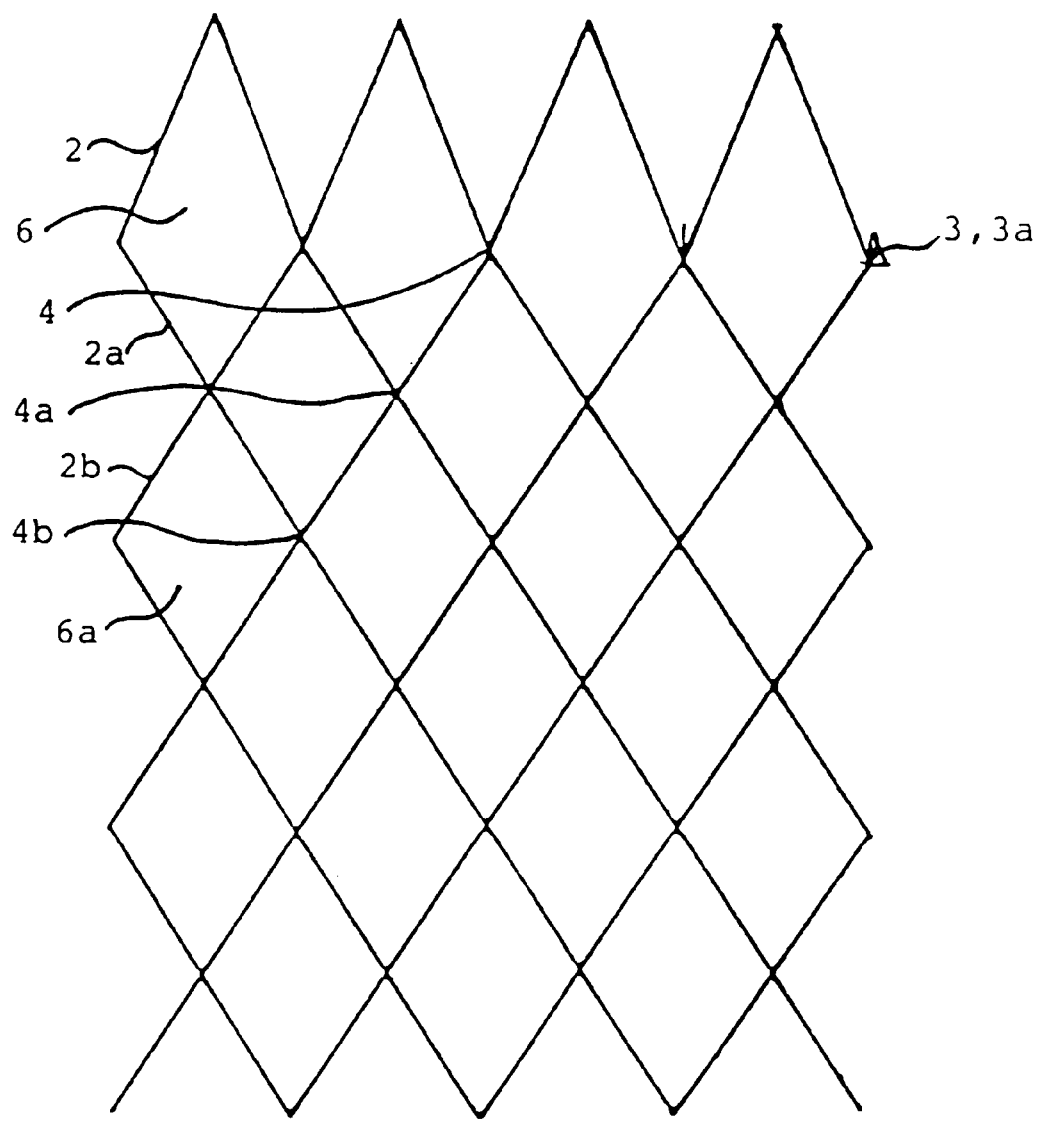
FIG. 3 is a highly diagrammatic representation of part of a stent for illustrating the design on the front ends.

FIG. 3 more particularly shows that the length of the ribs 2 of the outer or frontal meander areas is much greater than the ribs 2a, 2b in the main body 1a of the stent 1 according to the invention. The length of the end ribs 2 can be between 120 and 200% the ribs 2a to 2c of the main body. The length ratio can largely be chosen at random and is determined by the permitted expansion, the necessary stent length and the desired radial dilation of the end regions 1b, 1c over the main body 1a of the stent 1.

The stent 1 according to the invention is made from a nickel-titanium alloy, such as nitinol. It is produced in such a way that the metal plate or sheet is initially very accurately etched to the desired thickness, namely with a tolerance range of 0.001 mm. The parts forming the stent are then cut from a large-area plate. Said plate parts are then cut to form openings or slots in such a way that circumferentially adjacent slots are axially displaced by half their length. The cutting of the slots takes place by means of a laser. In the central area of each slot the latter is provided with an expansion, so that the material bounding the latter in the circumferential direction is reduced roughly to the width of the material remaining between the slots. These portions, if left standing, subsequently form the connecting portions 4, 4a, or the free spaces or gaps 5, 5a, etc. are created n their areas if the portions are removed. After cutting the slots the cutout parts are broken off and the slotted plate is deburred. The slotted plate is then bent to a cylinder, so that the lateral edges are in contact. Welds are then made on tongues or flaps, so that the stent is obtained in its low temperature position according to FIG. 1. This is followed by a heat treatment, in order to give the stent memory properties, so that after raising the temperature above a predetermined ambient temperature, which is well below the temperature of the human body, it can dilate to its high temperature position according to FIG. 2, which it reaches at a maximum temperature 35° C.

After producing and heat treating the stent in this way, the bridges are removed in the desired manner, so that the connecting areas or webs 4, 4a or free spaces 5, 5', 5a, etc. are formed, as described hereinbefore. This is followed by grinding and polishing, preferably in a rotary drum machine. The stents are then checked for dimensions, function and setting. This is followed by cleaning in an ultrasonic bath, initially with a soap solution, then with distilled water and finally with alcohol.

What is claimed is:

1. A method of dilating and keeping open a vessel comprising:

providing a stent having a body extending along a longitudinal axis of said stent, said body comprising material areas in the form of ribs and gaps in the form of free spaces between the ribs, said body having a radially contracted state for introduction of the stent into a vessel;

introducing the stent into a vessel; and radially expanding the stent to dilate and keep open the vessel;

wherein said step of providing includes forming said stent body such that said material areas are relatively thin and without material crossing points as in knitted and braided structures which give rise to a greater material thickness, and wherein said step of radially expanding includes expanding the stent to a radially expanded state having at least one end of opposite ends of the body along the longitudinal axis of the stent which has a greater diameter than the remaining body of the stent between said opposite ends with the ribs in the vicinity of said at least one end extending radially outwardly progressively in a direction along said longitudinal axis to said at least one end of the stent.

2. The method according to claim 1, wherein said step of radially expanding is not solely due to elastic properties of the stent and introduction of the stent into the vessel under radial tension.

3. The method according to claim 2, wherein said stent is constructed of a memory metal such that said stent, at a relatively low temperature can assume said radially contracted state for introduction into a vessel, and at a relatively higher temperature in said stent is radially expanded.

4. The method according to claim 3, wherein said stent self expands to said radially expanded state at said relatively higher temperature in said step of radially expanding.

5. The method according to claim 1, wherein said step of providing a stent includes forming said stent body such that said material areas are single layered.

6. The method according to claim 5, wherein said material areas have the same thickness, within a tolerance range of 0.001 mm.

7. The method according to claim 5, wherein said material areas are formed from a single sheet of metal.

8. The method according to claim 5, wherein said step of providing includes cutting slots in a flat metal sheet to form said gaps, bending said flat sheet to a cylindrical contour with marginal edges of said sheet adjacent one another, and welding the adjacent marginal edges of the sheet together to form said stent body with said material areas and gaps.

9. The method according to claim 1, wherein said ribs are extended further axially at said at least one end than within said remaining main body of the stent between said opposite ends.

10. Stent for dilating and keeping open a vessel, said stent comprising a body extending along a longitudinal axis of said stent, which body, in a radially contracted state, permits the stent to be introduced into a vessel and thereafter radially expanded to a radially expanded state in the vessel, wherein said body of the stent in the radially expanded state of the body having at least one end of the opposite ends of the body along the longitudinal axis of the stent which has a greater diameter than the main body of the stent intermediate said opposite ends, wherein said body has material areas in the form of ribs and gaps in the form of free spaces between the ribs, and wherein said material areas are relatively thin and without material crossing points as in knitted and braided structures which give rise to a greater material thickness, and wherein the ribs in the vicinity of said at least one end extend radially outwardly progressively in a direction along said longitudinal axis to said at least one end of the stent.

* * * * *